United States Patent

Lunsford et al.

[11] Patent Number: 5,993,384

[45] Date of Patent: *Nov. 30, 1999

[54] VESSEL ISOLATING RETRACTOR CANNULA AND METHOD

[75] Inventors: John P. Lunsford, San Carlos; Charles Gresl, Jr., San Francisco; Albert K. Chin, Palo Alto; John W. Davis; Tenny Chang, both of Mountain View; Jeffrey W. Baxter, San Jose, all of Calif.

[73] Assignee: Origin Medsystems, Inc., Menlo Park, Calif.

[*] Notice: This patent is subject to a terminal disclaimer.

[21] Appl. No.: 09/200,177

[22] Filed: Nov. 25, 1998

Related U.S. Application Data

[63] Continuation of application No. 09/102,723, Jun. 22, 1998, Pat. No. 5,895,353.

[51] Int. Cl.$^6$ .................................................. A61B 17/02
[52] U.S. Cl. ............................................ 600/209; 600/217
[58] Field of Search .................................. 600/208, 203, 600/206, 209, 210, 217, 236, 204

[56] References Cited

U.S. PATENT DOCUMENTS

| | | | |
|---|---|---|---|
| 3,313,294 | 4/1967 | Uddenberg | 600/209 |
| 3,857,386 | 12/1974 | Ashbell | 600/203 |
| 4,190,042 | 2/1980 | Sinnreich | 600/206 |
| 4,428,746 | 1/1984 | Mendez | 600/209 |
| 4,874,375 | 10/1989 | Ellison | 600/209 |
| 5,251,613 | 10/1993 | Adair | 600/205 |
| 5,271,385 | 12/1993 | Bailey | 128/20 |
| 5,275,608 | 1/1994 | Forman et al. | 600/205 |
| 5,337,736 | 8/1994 | Reddy | 600/217 |
| 5,374,277 | 12/1994 | Hassler | 606/207 |
| 5,450,842 | 9/1995 | Tovey et al. | 600/204 |
| 5,501,654 | 3/1996 | Failla et al. | 600/204 |
| 5,512,037 | 4/1996 | Russell | 600/206 |
| 5,564,615 | 10/1996 | Bishop et al. | 227/175.1 |
| 5,588,581 | 12/1996 | Conlon et al. | 227/176.1 |
| 5,626,587 | 5/1997 | Bishop et al. | 606/143 |
| 5,634,584 | 6/1997 | Okorocha et al. | 227/176.1 |
| 5,662,662 | 9/1997 | Bishop et al. | 606/143 |
| 5,673,840 | 10/1997 | Schulze et al. | 227/175.2 |
| 5,680,982 | 10/1997 | Schulze et al. | 227/175.1 |
| 5,690,606 | 11/1997 | Sioman | 600/209 |
| 5,702,408 | 12/1997 | Wales et al. | 606/139 |
| 5,704,534 | 1/1998 | Huitema et al. | 227/175.1 |
| 5,713,505 | 2/1998 | Huitema | 227/179.1 |
| 5,716,352 | 2/1998 | Viola et al. | 606/1 |
| 5,938,620 | 9/1996 | Hecke'e et al. | 600/209 |

*Primary Examiner*—Paul J. Hirsch
*Attorney, Agent, or Firm*—Fenwick & West LLP

[57] ABSTRACT

A retractor and a surgical tool are positioned within a cannula, and a dissection cradle of the retractor is positioned at the distal end of the cannula. The retractor includes a first portion with an axis approximately parallel to the axis of the cannula and a second portion with an axis at an angle to the axis of the cannula. The dissection cradle is located at the distal end of the second portion of the retractor, and may include two substantially parallel, spaced legs with the retractor shaped in a loop between and in a plane skewed relative to the axis of the legs, and with the loop directed away from the surgical tool. Thus, in operation, when the surgeon locates a vein and side branch of interest, the surgeon extends the retractor to cradle the vein in the dissection cradle. Once cradled, the retractor may be fully extended to urge the vein away from the axis of the cannula isolate the side branch for exposure to the surgical tool. In another embodiment, the cannula includes a sheath which encases the curved, resilient retractor at a first position to retain the retractor in substantially straight orientation, and which encases the retractor at a second position that allows the retractor to extend at an angle relative to the axis of the cannula.

20 Claims, 8 Drawing Sheets

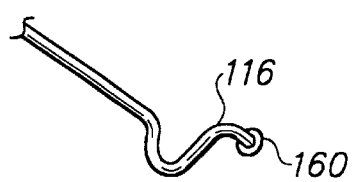
FIG. 9F
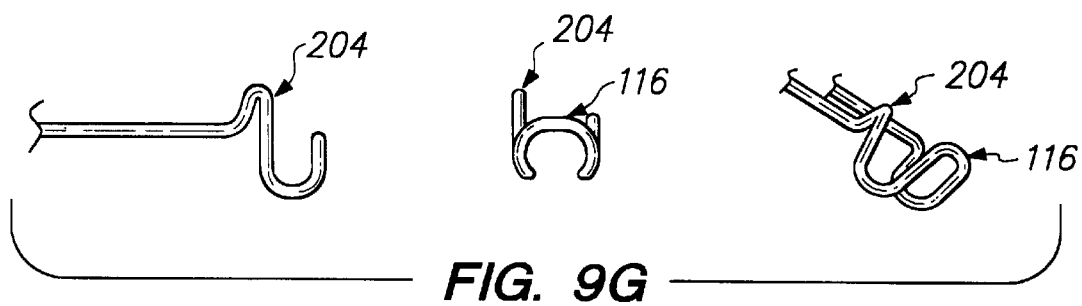
FIG. 9G
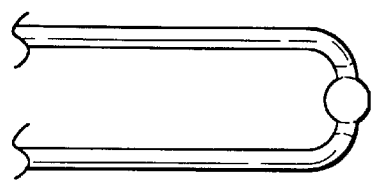 
FIG. 10A      FIG. 10B
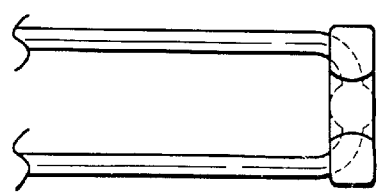 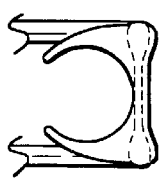
FIG. 10C      FIG. 10D

VESSEL ISOLATING RETRACTOR CANNULA AND METHOD

RELATED APPLICATIONS

This is a continuation of application Ser. No. 09/102,723 filed on Jun. 22, 1998, now U.S. Pat. No. 5,895,353 which is incorporated by reference herein in its entirety.

FIELD OF THE INVENTION

This invention relates to a cannula used for vein retraction, and more particularly to a cannula and method that includes a vein retractor having a first portion that is approximately parallel to the axis of the cannula and a second portion that is positioned at an angle with respect to the axis of the cannula.

BACKGROUND OF THE INVENTION

Certain cannulas have surgical tools located within the cannula for performing surgical operations on a vessel of interest. The cannula is inserted into a surgical site with the distal end of the cannula positioned near the vessel of interest. An endoscope positioned within the cannula allows the surgeon to view the target area and allows the surgeon to position the surgical tool correctly.

However, the surgical tool may be inadequate to safely and effectively perform its operation. For example, if the target vessel is a side branch or tributary of a vein such as a saphenous vein the surgical tool may sever or damage the vein while being used to cut the side branch. Thus, there is needed a cannula which is able to isolate the target vessel of interest to allow the surgical tool to perform safely and effectively.

SUMMARY OF THE INVENTION

In accordance with the present invention, a retractor is positioned within a cannula with a dissection cradle end of the retractor positioned at the distal end of the cannula The retractor includes a first portion that has an axis approximately parallel to a central axis of the cannula, and a second portion that has an axis which is at an angle with respect to the central axis of the cannula. The dissection cradle is located at the distal end of the second portion of the retractor. In another embodiment, the retractor includes two legs having a substantially parallel axis that selectively protrude from the distal end of the cannula to support the dissection cradle formed in the shape of a loop that is positioned in a plane skewed relative to the axis of the legs, with a bottom of the loop directed away from the cannula. Thus, in operation, when the surgeon locates a vein and side branch of interest, the surgeon extends the retractor to cradle the vein in the dissection cradle. Once cradled, the retractor may be fully extended, pulling the vein away from the axis of the cannula causing the side branch to be isolated and exposed to a surgical tool. The surgical tool may then be extended from within the cannula to operate on the isolated and exposed side branch.

In another embodiment, the top of the loop of the dissection cradle is flat and in, allowing atraumatic support of the vein, and minimizing contact between the retractor and the surgical tool. In yet a further embodiment, the retractor includes a single leg with the loop formed by the one leg of the retractor, and with a stopper coupled to the distal end of the retractor. In still another embodiment, the cannula comprises a sliding tube which encases the retractor, and in a first position is extended out to encase the second portion of the retractor, and in a second position is extended to encase only the first portion of the retractor. In response to being in the first position, the second and first portions of the retractor are both approximately parallel to the axis of the cannula. In the second position, the second portion of the retractor is at an angle to the axis of the cannula.

BRIEF DESCRIPTION OF THE DRAWINGS

FIG. 7b is a side view of the retractor 112 of FIG. 7a.

FIG. 9f illustrates multiple views of a fifth alternate embodiment of cradle 116.

FIG. 9g illustrates multiple views of an embodiment of cradle 116 having a spur.

FIG. 10a illustrates a top view of an embodiment of the cradle 116 of FIG. 9c without a "C" ring.

FIG. 10b illustrates a side view of the cradle 116 of FIG. 10a.

FIG. 10c illustrates a top view of the cradle 116 of FIG. 9c with the "C" ring attached.

FIG. 10d illustrates a side view of the cradle 116 of FIG. 10c.

DETAILED DESCRIPTION OF THE PREFERRED EMBODIMENTS

Figure 1:
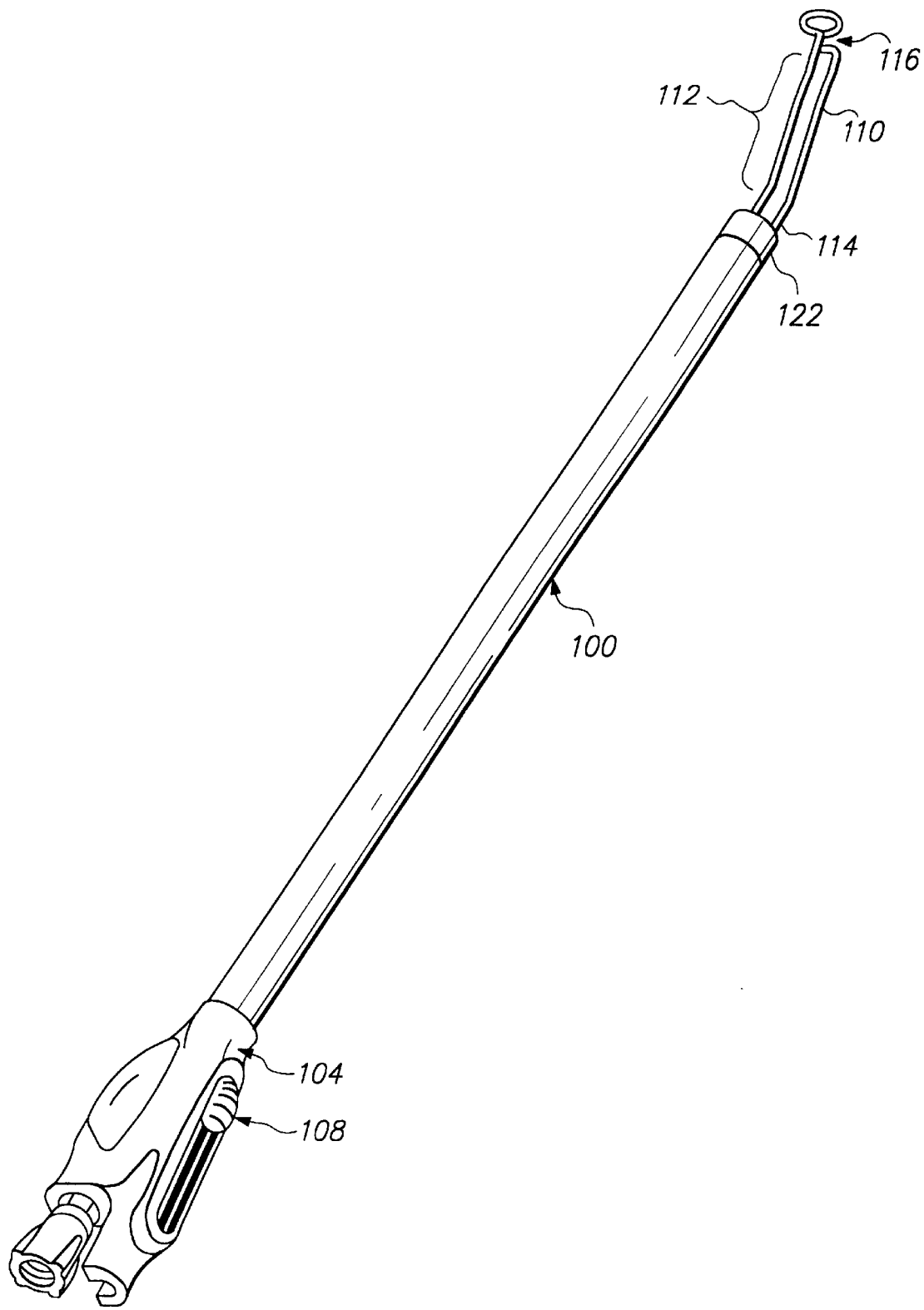
FIG. 1 is a perspective view of a preferred embodiment of cannula 100 showing retractor 112 in an extended position.

FIG. 1 illustrates a perspective view of a preferred embodiment of cannula 100 showing retractor 112 in an extended position. Cannula 100 includes an outer housing 102 of bioinert material such as polymed UD that may be approximately 12" to 18" in length. The proximal end of the cannula 100 is disposed in handle 104 that includes a button 106 which is coupled to retractor 112 for controlling the translational movement of retractor 112, as described in more detail below.

Figure 2A:
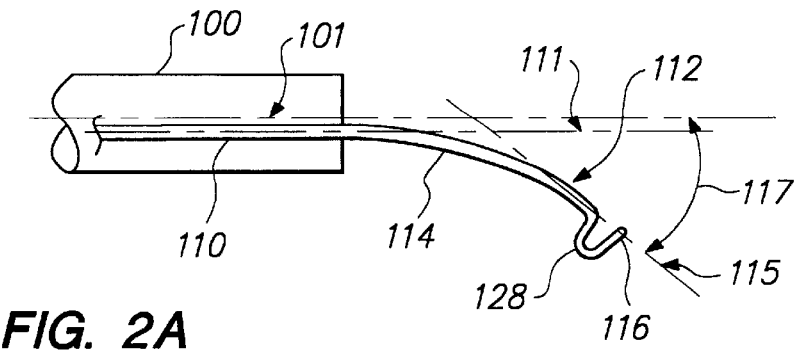
FIG. 2a is a cut-away side view of retractor 112 and cannula 100.

The distal end of the cannula houses a retractor 112, and optionally an endoscope 126 and a surgical tool 120, described below. FIG. 2a illustrates the retractor 112 in more detail. In one embodiment, retractor 112 is formed of resilient wire which has a smooth bend intermediate to a first portion 110 and a second portion 114 of the retractor. The retractor 112 is described as having two portions for ease of description, although the retractor 112 may be formed as an integrated structure. However, retractor 112 may also be manufactured from two separate portions 110, 114 that are coupled together. The first portion 110 of the retractor 112 is positioned within the cannula 100 with the axis 111 of the first portion 110 approximately parallel to the axis 101 of the cannula 100. The second portion 114 is positioned to bend away from the central axis 101 of the cannula The angle 117 of displacement between the axis 115 of the second portion and the central axis 101 of cannula 100 may be any angle from zero to 180 degrees. The second portion 114 includes a dissection cradle 116 at the distal end of the second portion 114. The retractor 112 may be formed of bioinert material such as stainless steel, or a polymer such as nylon or polyetherimide, or other appropriately strong and springy plastic. In one embodiment, the retractor 112 includes a coating for lubrication, insulation, and low visual glare using, for example, parylene or nylon 11.

Figure 2B:
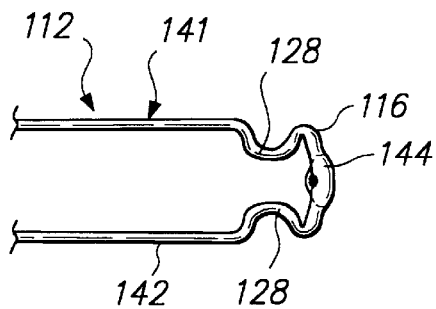
FIG. 2b is a top view of retractor 112.

FIG. 2b illustrates the retractor 112 formed with two legs. The legs 141, 142 of the retractor 112 at the distal end form the dissection cradle 116 in a loop or "U" shape, as shown in FIG. 2a. The top portion 144 of the U-shaped bend is preferably flattened to provide additional surface area for atraumatically supporting a vein 118 or vessel of interest. The side arches 128 of the dissection cradle 116 are used for skeletonizing or dissecting the vein from the surrounding tissues, as well as acting as walls to keep the vessel captured within the arch. The several embodiments of dissection cradle 116 are described in more detail below.

Figure 3A:
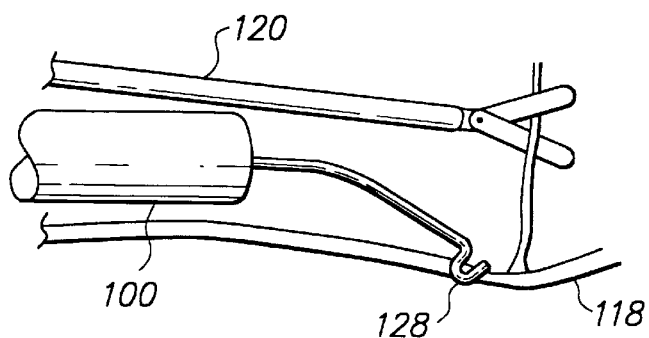
FIG. 3a is a perspective side view of cannula 100 with a saphenous vein positioned within the cradle 116.

FIG. 3a illustrates a perspective view of the cannula 100 in accordance with the present invention with the retractor fully extended, holding a saphenous vein 118, and also illustrates an external surgical tool 120 disposed adjacent the cannula 100 for performing a surgical operation, for example, severing a tributary or side branch of the vein 118. The vein is positioned within the side arches 128 of the cradle 116. The dissection cradle 116 may be used to cradle a vein, vessel, tissue or organ of interest, and surgical tool 120 may be any surgical tool suitable for performing a surgical procedure near the dissection cradle 116.

Figure 3B:
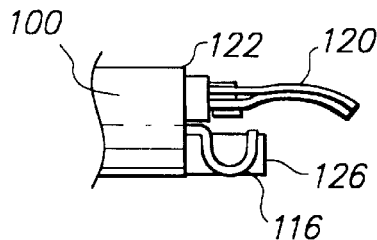
FIG. 3b is a perspective side view of the distal end 122 of cannula 100 in an embodiment in which an endoscope 126 and a surgical tool 120 are present and partially extended.
Figure 3C:
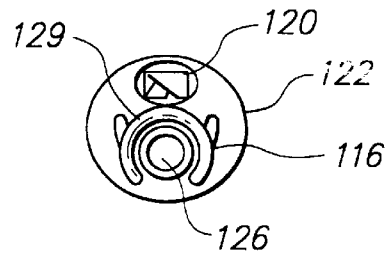
FIG. 3c is a front view of the distal end 122 of cannula 100 in which the surgical tool 120 and the retractor 116 are partially extended, and an endoscope 126 is present.

FIG. 3b illustrates a perspective view of cannula 100 in an embodiment in which the surgical tool 120 is positioned within the cannula 100, and an endoscope 126 is present. In this embodiment, cradle 116 preferably overlays the endoscope 126 with sufficient clearance to facilitate relative movements thereof. However, the endoscope may also be located adjacent the surgical tool 120. In one embodiment, endoscope 126 is positioned with cannula 100 to allow a clear field of view upon extension of the retractor 112. Surgical tool 120 is illustrated as scissors, used to sever a tributary or side branch of a saphenous vein 118. In this embodiment, surgical tool 120 is maximally displaced from the cradle 116 at the cannula end 122. More specifically, as shown in FIG. 3c, the "U"-shaped loop 129 of the cradle 116 is closest to the surgical tool 120. This ensures that a vein 118 or other tissue of interest is retracted away from the surgical tool 120 to facilitate manipulating the surgical tool 120 relative to the side branch or other tissue.

Figure 4A:
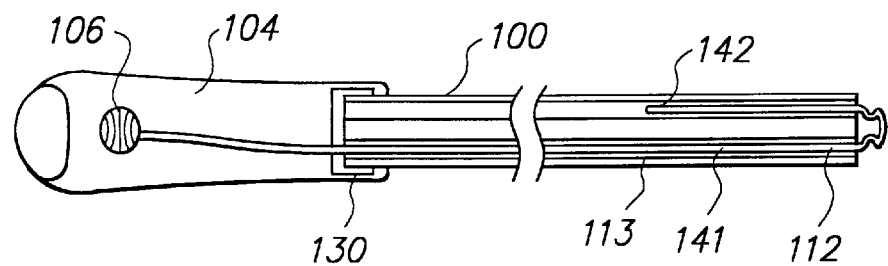
FIG. 4a is a cut-away top view of cannula 100.
Figure 4B:
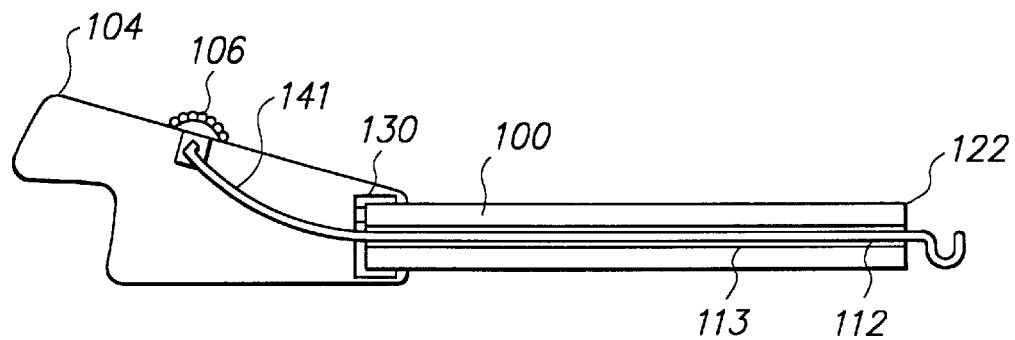
FIG. 4b is a cut-away side view of cannula 100.

FIG. 4a is a cut-away top view of cannula 100. The retractor 112 is slidably positioned within minor lumens 113 along the length of the cannula 100 within close tolerances in order to position the retractor 112 stably within the cannula 100. For example, in one embodiment retractor legs 141, 142 are approximately 0.045 inches in diameter and the lumens 113 encasing the legs 141, 142 are approximately 0.080 inches in diameter, as friction between the legs of the retractor 12 and the lumens 113 holds the retractor stably within the cannula. This configuration restricts rotational movement of the retractor to provide more stable retraction as compared with conventional retractors. The legs 141, 142 of the retractor 112 are formed of flexible, resilient material and are retained within the lumen 113 in substantially straight or flat orientation, but may return to a material bend or curve, as illustrated in FIG. 5a, as the retractor 112 is extended from the distal end of the cannula 100.

The leg 141 of the retractor 112 passes through a sliding gas or fluid seal 130 at the proximal end of the lumen 113. The leg 141 of the retractor 112 passes out of the cannula 100 and into handle 104 for attachment to a slider button 106 for facilitating translational movement of the retractor 112 from the proximal or handle end of the cannula 100. However, other types of control devices such as knobs, grips, finger pads, and the like may be linked in conventional ways to the retractor 112 in order to manually control the translational movement of retractor 112. In one configuration, the proximal end of leg 141 is bent relative to the axis of the cannula, and the button 106 is attached to the bent position of the leg 141 to facilitate moving the button 106 and the retractor 112 translationally under manual control. The button 106 preferably includes lateral grooves to prevent finger or thumb slippage during sliding manipulation of the retractor 112.

Thus, in the operation of a preferred embodiment, a user actuates the slider button 106 to extend retractor 112 out of the lumen 113 at the distal end of the cannula 100. In one embodiment, the resilient retractor 112 is formed in a smooth bend, as shown in FIG. 2a and gradually deflects away from the central axis 101 of the cannula 100 as the retractor is extended. Upon encountering the target vessel or tissue of interest, the vessel is restrained in the cradle 116, and a lateral resilient force is exerted on the target vessel in a direction away from the cannula. The vessel is thus pushed away from the axis of the cannula 100, isolating it from surrounding tissue or adjacent vessels such as tributaries or side branches. As a tributary is thus isolated, a surgical tool 120 such as cauterizing scissors may be safely employed to operate on the tributary without harming the saphenous vein 118. When retracted into the cannula 100, the retractor 112 is again resiliently straightened or flattened.

Figure 5A:
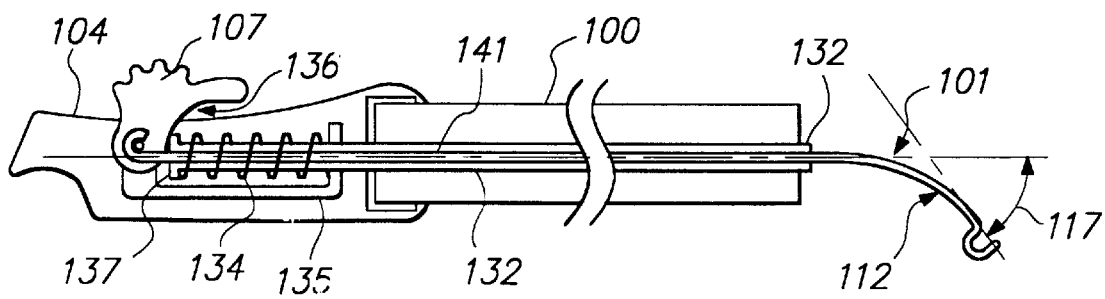
FIG. 5a is a cut-away view of a sliding tube embodiment of cannula 100 in a first position.
Figure 5B:
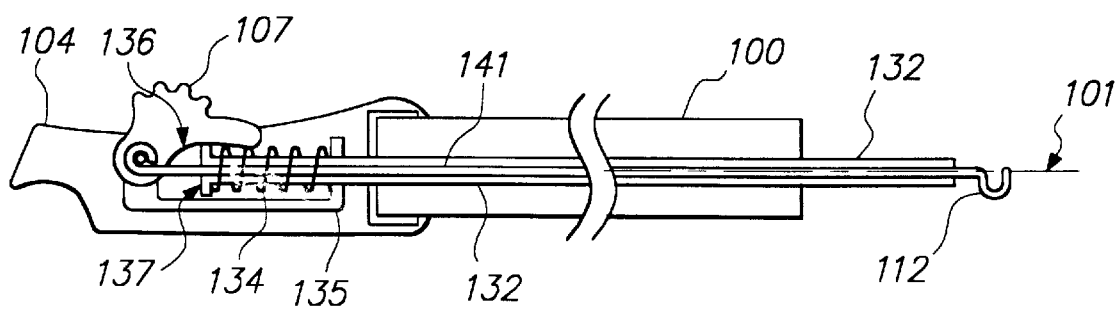
FIG. 5b is a cut-away view of the sliding tube embodiment of FIG. 5a in a second position.

In an alternate embodiment as illustrated in FIGS. 5a and 5b, a sliding tube 132 is added to provide operational versatility to cannula 100. In a first position, the sliding tube 132 is retracted and the retractor 112 protrudes from the distal end at an angle with respect to the central axis 101 of the cannula 100. In a second position, the sliding tube 132 is extended out, temporarily straightening the retractor 112. As illustrated in FIG. 5a, a sliding tube 132, in a first position encases the retractor 112 up to the point at which the retractor 112 curves away from the central axis 101 of the cannula thus allowing the retractor 112 to displace and isolate a target vessel. The proximal end of the sliding tube 132 is linked to button 107 for translationally moving retractor 112 as well as actuating the sliding tube 132. In one embodiment, as illustrated in FIG. 5a, the sliding tube 132 is in a first position with the button 107 in an upright position. A spring 134 is coupled between a support structure 135 and the proximal end 137 of the sliding tube 132. In the first position of sliding tube 132, the spring 134 is extended fully and exerts little or no force on the sliding tube 132. Of course, sliding tube 132 may be manually manipulated without linkage to a button 107.

To extend the sliding tube 100, button 107 is pushed down. As illustrated in FIG. 5b, the button 107 has a cam surface 136 which pushes on the proximal end 137 of the sliding tube 132 as the button 107 is pressed. The sliding tube 132 is pushed forward. overcoming the resilient force of spring 134, to encase the retractor 112 and decrease angle 117 between the distal end of the retractor 112 and the central axis 101 of the cannula 100. Upon releasing the button 107, the spring force urges the proximal end 137 of the sliding tube 132 back toward the first position against button 107. The sliding tube 132 is formed of material having sufficient strength to force the retractor 112 to straighten out the angle 117, and the retractor 112 is formed of resilient material having a sufficient flexibility to straighten out the angle 117 in response to a tube 132 being slid over the retractor 112, but having sufficient rigidity to cradle and dissect a target vessel. Resiliency of the retractor 112 ensures return to the downwardly-curved shape after being released from tube 132. Thus, in accordance with this embodiment, a user may employ the curved retractor for certain applications and employ the straightened form for other applications. A manual actuator may be configured in other ways than button 107 to extend the sliding tube 132 in response, for example, to being pulled up instead of pushed down.

Figure 6A:
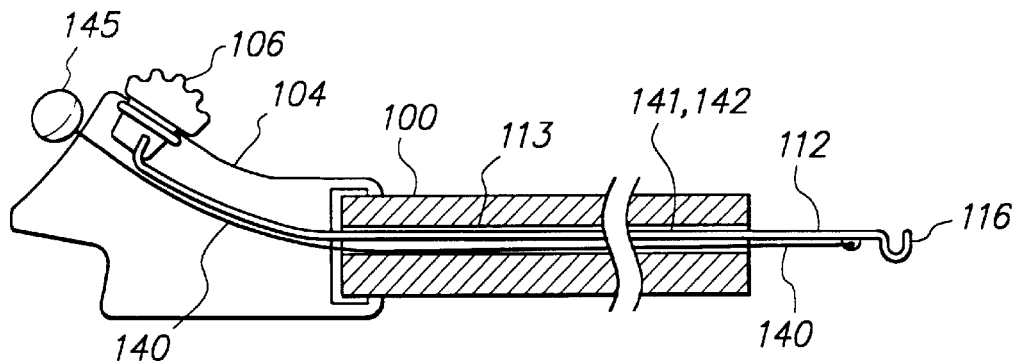
FIG. 6a is a cut-away view of an embodiment of cannula 100 having an angling device 140.
Figure 6B:
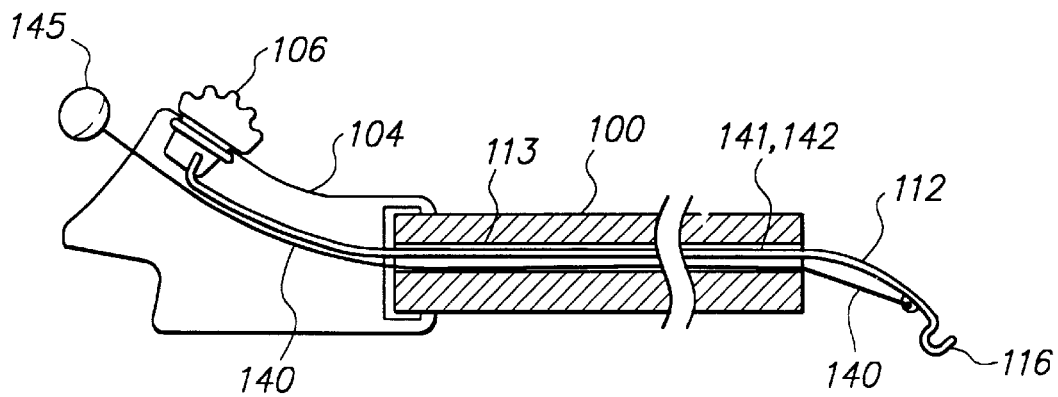
FIG. 6b is a cut-away side view of the apparatus illustrated in FIG. 6a in which the retractor 112 is extended and the angling device 140 is actuated.

Another embodiment employs a retractor 112 which has a naturally straight shape. As illustrated in FIGS. 6a and 6b, an angling device 140 is disposed between the distal end of the retractor 112 and the proximal end of the cannula. The angling device 140 may be positioned within the same lumens 113 as the retractor 112 and preferably may comprise two wires coupled to points below the cradle 116 of the retractor 112 substantially in parallel positions on each of the legs 141, 142.

Figure 6C:
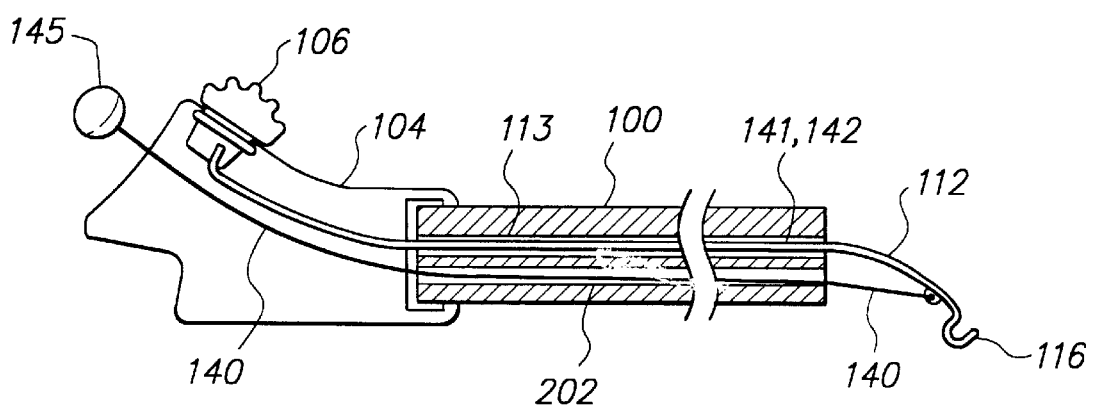
FIG. 6c is a cut-away side view of the angling device embodiment in which the angling device 140 is in a separate lumen from the retractor 112.

Upon extending the retractor 112 using button 106, the angling device 140 is extended with the retractor 112. The angling device 140 is coupled to a handle 145 at the proximal end of the cannula 100 to facilitate establishing an angle in the retractor 112 by pulling with a backward force on the angling device 140. As illustrated in FIG. 6b, after the retractor 112 is extended, the angling device 140 is actuated and a bend is created in the retractor 112 as the backward force exerted on the distal end of the retractor is exerted against the relatively fixed position of the retractor legs 141, 142 disposed within the lumens 113. As shown in FIG. 6c, the angling device 140 may also be located in a separate lumen 202 from the retractor 112 with part of the angling device 140 positioned outside of the cannula 100 when the retractor 112 is in the retracted position.

Figure 7A:
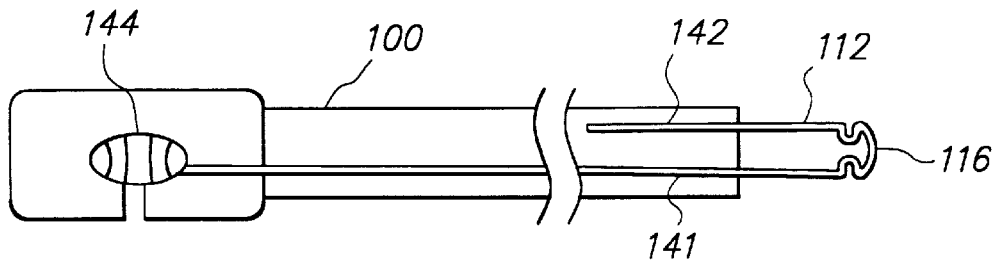
FIG. 7a is a cut-away side view of a twistable retractor 112 in a straight position.
Figure 7C:
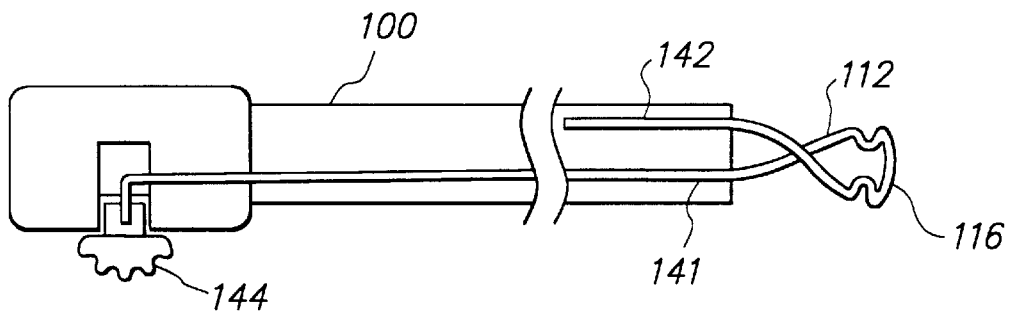
FIG. 7c is a cut-away side view of twistable retractor 112 in a crossed position.
Figure 7B:
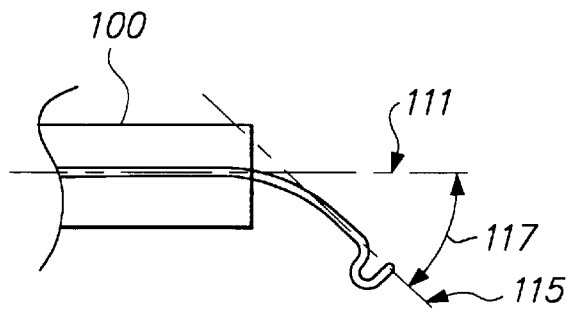
Figure 7D:
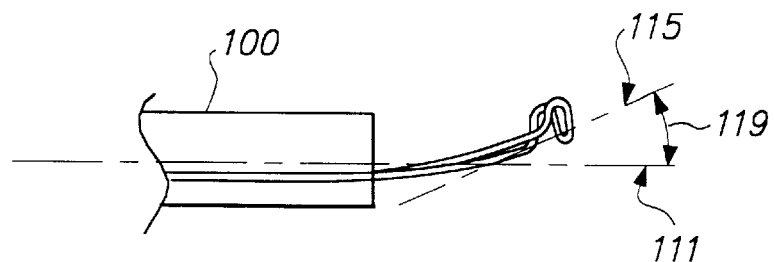
FIG. 7d is a side view of the retractor 112 of FIG. 7c.

FIG. 7a illustrates another embodiment of cannula 100 in which the retractor 112 is pre-formed with one leg 141 of the retractor 112 bent at an angle at its proximal end skewed to the axis of the distal end of the other leg 142. The bent portion of the leg 141 may be linked to a sliding knob 144 for convenient manual manipulation of this embodiment of the invention. Upon sliding the knob 144, the leg 142 coupled to knob 144 is twisted rotationally. The two legs 141, 142 of retractor 112 are coupled together via cradle 116. The axis of the second portion of the retractor 112 in the first position is at a first angle 117 to the axis of the cannula 100, as shown in FIG. 7b. As knob 144 is moved, leg 141 is rotated and crosses under leg 142, as shown in FIG. 7c. This causes cradle 116 to flip 180 degrees and bends the retractor 112 at a second angle 119, as shown in FIG. 7d. Thus, if a vessel is disposed on one side of cradle 116 or cannula 100 while the retractor 112 is in the first position, then upon rotating the knob 144, the vessel is transported to the other side of the cannula 100. This allows the user to isolate the vessel by simply actuating knob 144.

Figure 8A:
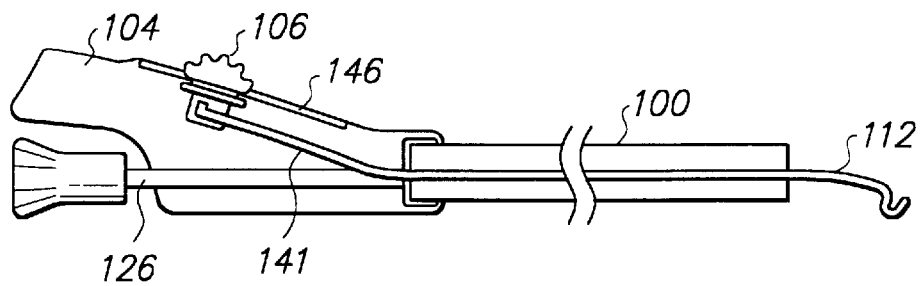
FIG. 8a is a cut-away side view of the handle 104.
Figure 8B:
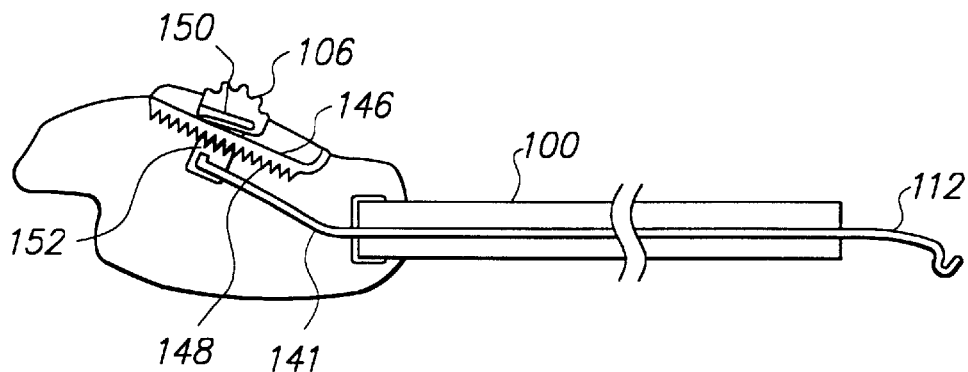
FIG. 8b is a cut-away side view of an alternate embodiment of handle 104.

FIG. 8a illustrates a cut-away side view of button 106 on the handle 104 of cannula 100, with an endoscope 126 positioned within cannula 100. As mentioned above, button 106 is coupled to one leg 141 of the proximal end of retractor 112. Sliding the button 106 in groove 146 translationally moves the retractor 112. Groove 146 is preferably minimally wider than the shaft of button 106 to minimize excessive horizontal movement of button 106 while still allowing smooth translational movement of button 106. As illustrated in FIG. 8b, the button 106 may include locking or ratcheting teeth 152 to give tactile feedback of its location, and to positively retain the button and the associated leg 141 in an extended or retracted position. Several mating teeth 148 are located underneath groove 146, and a spring member 150 is attached to button 106 to exert pressure against the base of groove 146, to engage mating teeth 148, 152. When a force is applied on the top of button 106, the interlocking sets of teeth are disengaged and button 106 can move freely. Upon achieving the desired extension or retraction of the leg 141, button 106 is released and is retained place by the engaged teeth 148, 152.

Figure 9A:
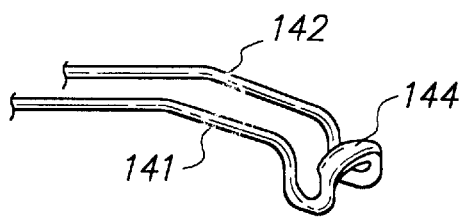
FIG. 9a is a side view of cradle 116.

FIG. 9a illustrates a top view of cradle 116 in an embodiment in which the cradle 116 is formed by two legs 141, 142 of retractor 112. The distal end of the legs form "U"-shaped side guides. The top 144 of the distal portion of the "U" is preferably flattened. This provides atraumatic support for the target vessel retained within cradle 116. Additionally, by minimizing the thickness of distal portion 144, contact with other devices in close proximity with retractor 112 is minimized.

Figure 9B:
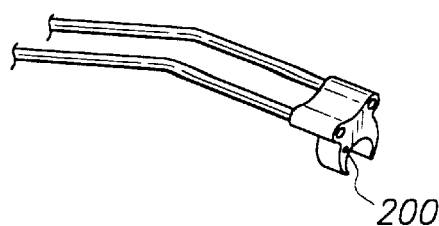
FIG. 9b illustrates a first alternate embodiment of cradle 116.

The cradle 116 may have other effective shapes, for example, as illustrated in FIG. 9b in which a "C" ring element is attached to legs of the cradle 116. The "C" ring may have a small hole 200 in one side with an axis approximately parallel to the axis of the retractor 112. This hole 200 is used to hold suture or other ligating materials, and may also be used as a knot pusher. As shown in FIGS. 10a and 10b, in an alternate embodiment of the embodiment of FIG. 9b, the retractor 112 is formed and flattened and a "C"-shaped ring is coupled to the retractor 112 by, for example, gluing or molding the "C" ring to the distal end of the retractor 112, as shown in FIG. 10c and 10d.

Figure 9C:
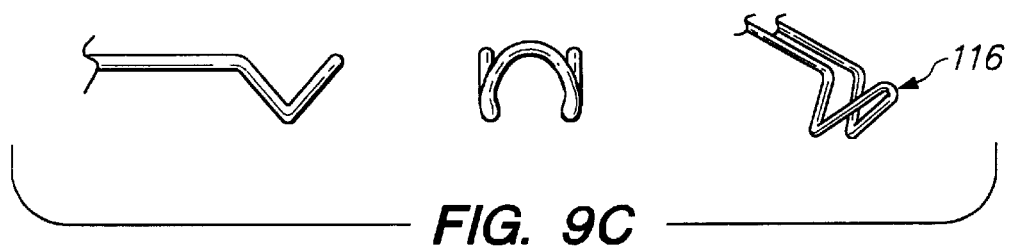
FIG. 9c illustrates multiple views of a second alternate embodiment of cradle 116.
Figure 9D:
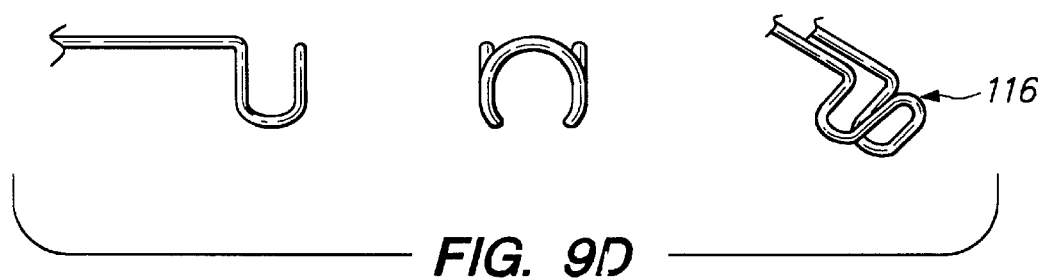
FIG. 9d illustrates multiple views of a third alternate embodiment of cradle 116.
Figure 9E:
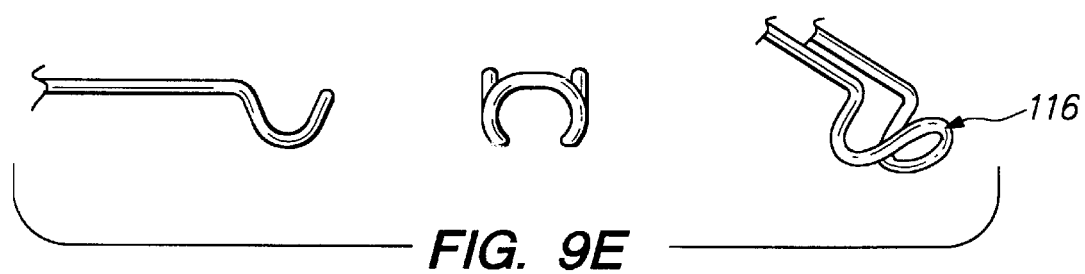
FIG. 9e illustrates multiple views of a fourth alternate embodiment of cradle 116.

Referring back to FIGS. 9c, 9d, and 9e, the side guides of the cradle may include a loop 129 in a "V" shape, an arced "U" shape, or a semi-circular shape. In one embodiment, as illustrated in FIG. 9f, the retractor 112 has only one leg 141, and the cradle 116 is formed by the leg 141. A stopper 160 is coupled to the end of the leg 141 to serve as a guide to retain the target vessel, and add a blunt surface to the end of the wire, for example, for pushing and probing tissue. FIG. 9g illustrates a retractor 112 having a spur 204 formed in one or both legs 141, 142 for allowing the retractor 112 to be used for dissection. Sinusoidal, half-sinusoidal, and other geometric configurations may be used equally effectively as the shape of loop 129 in accordance with the present invention.

We claim:

1. A surgical apparatus comprising:
   an elongated cannula having a central axis between distal and proximal ends, and
   a retractor, slidably supported by the cannula for translational movement substantially aligned with the central axis and having a first portion disposed near the proximal end of the cannula and a second portion disposed near the distal end of the cannula, the second portion having a dissection cradle positioned at the distal end of the second portion, the dissection cradle being positioned in a plane which is substantially parallel to the central axis of the cannula in a retracted position, and being positioned in a plane skewed relative to the central axis of the cannula upon slidable extension thereof forward of the distal end of the cannula.

2. The apparatus of claim 1 wherein the retractor comprises two legs, and the dissection cradle is formed between the two legs having substantially parallel axes at the distal end of the retractor in the shape of a loop positioned in a plane skewed relative to the axes of the legs, and a portion of the loop between the two legs is directed away from the central axis of the cannula.

3. The apparatus of claim 2 in which the portion of the retractor forming a top of the loop of the dissection cradle is substantially flat to atraumatically support tissue.

4. The apparatus of claim 1 wherein an angle between the dissection cradle and the central axis of the cannula is between approximately zero and approximately ninety degrees.

5. The apparatus of claim 2 wherein the loop has arcs which form substantially a "U" shape, and the arcs are of substantially similar size, and tissue to be displaced upon extension of the retractor is cradled between the arcs of the "U"-shape.

6. The apparatus of claim 2 wherein the loop has arcs which form substantially a "V" shape, and the arcs are of substantially similar size, and tissue to be displaced upon extension of the retractor is cradled between arcs of the "V"-shaped loop portion.

7. The apparatus of claim 2 wherein the loop has arcs which form substantially a "C" shape, and the arcs are of substantially similar size, and tissue to be displaced upon extension of the retractor is cradled between arcs of the "C"-shaped loop portion.

8. The apparatus of claim 2 wherein the legs are spaced apart and the loop is disposed between the legs near distal ends thereof to allow tissue to be displaced to be cradled within the legs.

9. The apparatus of claim 8 wherein the loop includes a body having arms forming the loop, and including a hole disposed through an arm in substantial alignment with a leg for holding surgical material therein.

10. The apparatus of claim 1 further comprising:
    a button coupled to the proximal end of the retractor and positioned near the proximal end of the cannula for translationally moving the retractor relative to the cannula in response to manual actuation of the button.

11. The apparatus of claim 10 wherein the button further comprises ratcheting teeth for mating with corresponding teeth disposed relative to the proximal end of the cannula for retaining the retractor at a preferred extension relative to the distal end of the cannula and for providing tactile feedback of the translational movement of the retractor relative to the cannula.

12. The apparatus of claim 1 comprising:
    an angling device having a distal end coupled to the retractor near the distal end thereof;
    an actuating knob coupled to a proximal end of the angling device for bending the dissection cradle away from the axis of the cannula in response to manipulation of the knob relative to the cannula.

13. The apparatus of claim 1 comprising:
    a surgical tool positioned within the cannula near the distal end of the cannula having an operable end positioned near the distal end of the cannula controlled from near the proximal end of the cannula, and
    the dissection cradle projects away from the surgical tool upon extension of the retractor relative to the cannula.

14. The apparatus of claim 1 comprising:
    an endoscope, positioned within the cannula near the distal end of the cannula for transmitting images of a surgical site to a remote location within a field of view; and
    the retractor bends away from the field of view of the endoscope upon extension of the retractor relative to the cannula.

15. A surgical apparatus comprising:
    an elongated cannula having a central axis between distal and proximal ends, and a retractor, wherein the retractor is located eccentric the central axis of the cannula, the retractor further comprising:
    a first leg, having an axis substantially parallel to the central axis of the cannula, and having a distal end disposed forward of the end of the cannula;
    a second leg, having an axis substantially parallel to the central axis of the cannula, and spaced from the first leg; a dissection cradle attached to the distal ends of the first and second legs; and the second leg having a proximal end that is unattached to the proximal end of the cannula for selective rotation of the proximal end of the second leg to rotate the dissection cradle responsive to rotation of the proximal end of the second leg, and to cause the dissection cradle to project away from the central axis of the cannula.

16. A surgical apparatus comprising:
    an elongated cannula having a central axis between distal and proximal ends;
    a retractor, slidably supported by the cannula for translational movement substantially aligned with the central axis and having a first portion disposed near the proximal end of the cannula and a second portion disposed near the distal end of the cannula, the second portion having a dissection cradle positioned at the distal end of the second portion and projecting away from the central axis of the cannula upon slidable extension thereof forward of the distal end of the cannula; and
    a tube having a first end positioned near the proximal end of the cannula and a second end positioned near the distal end of the cannula and being slidably disposed on the cannula to encase the retractor in a first position and to encase a portion of the retractor in a second position; the retractor having a resilient shape and being responsive to the tube in the first position to extend forward of the distal end of the cannula in approximately parallel orientation relative to the central axis of the cannula, and being responsive to the tube in the second position to extend forward of the distal end of the cannula at an angle with respect to the central axis of the cannula.

17. The apparatus of claim 16 further comprising:

a handle disposed on the proximal end of the cannula and including an actuator button, linked to the proximal end of the sliding tube and having a first operating state in which the sliding tube is extended towards the distal end of the cannula, and having a second operating state in which the tube is retracted relative to the distal end of the cannula.

18. A method of surgery with a cannula including a retractor having a dissection cradle positioned on the distal end of the retractor, the dissection cradle being positioned in a plane which is substantially parallel to the central axis of the cannula in a retracted position, and positioned in a plane skewed relative to the central axis of the cannula upon slidable extension thereof forward of the distal end of the cannula, the method comprising:

resiliently supporting the retractor on the cannula for selectively translating the retractor relative to the cannula;

inserting the distal end of the cannula within a surgical site; and translating the retractor relative to the cannula in response to manipulation of the proximal end of the retractor relative to a central axis of the cannula for selectively extending the distal end of the retractor to position the dissection cradle into a plane which is skewed relative to the central axis of the cannula.

19. A surgical apparatus comprising:

an elongated cannula having a central axis between distal and proximal ends, and a retractor, slidably supported by the cannula for translational movement substantially aligned with the central axis and having a first portion disposed near the proximal end of the cannula and a second portion disposed near the distal end of the cannula, the second portion having a dissection cradle positioned at the distal end of the second portion, and the intersection between the first and second portion having a predefined bend to project the dissection cradle away from the central axis of the cannula upon slidable extension of the dissection cradle forward of the distal end of the cannula.

20. The apparatus of claim 1 comprising:

an angling device comprising:

a first wire, having a distal end coupled to a first leg of the dissection cradle; and a second wire, having a distal end coupled to a second leg of the dissection cradle;

an actuating knob, coupled to the proximal ends of the first and second wires, for bending the dissection cradle away from the axis of the cannula in response to manipulation of the knob relative to the cannula by increasing the tension in the first and second wires.

* * * * *